United States Patent [19]

Lang et al.

[11] Patent Number: 4,814,162
[45] Date of Patent: Mar. 21, 1989

[54] COSMETIC COMPOSITIONS CONTAINING HYDROXYL DERIVATIVES OF DIBENZOYLMETHANE AND THEIR USE IN PROTECTING THE SKIN AGAINST ULTRAVIOLET RAYS AND DERIVATIVES FOR USE THEREIN

[75] Inventors: Gerald Lang, Saint Gratien; Alain Malaval, Marly la Ville; Madeleine Leduc, Paris, all of France

[73] Assignee: L'Oreal, Paris, France

[21] Appl. No.: 798,364

[22] Filed: Nov. 18, 1985

[30] Foreign Application Priority Data

May 20, 1981 [FR] France .................. 81 10063

[51] Int. Cl.$^4$ .................. A61K 7/42; A61K 7/44; A61K 9/10; A61K 9/12
[52] U.S. Cl. .................. 424/47; 8/405; 8/406; 424/DIG. 4; 424/59; 424/60; 424/61; 424/63; 424/64; 424/70; 514/937; 514/943; 514/944; 514/969; 514/972; 568/337
[58] Field of Search .................. 424/59, 60, 47; 568/337

[56] References Cited

U.S. PATENT DOCUMENTS

| | | | |
|---|---|---|---|
| 3,665,074 | 5/1972 | Brandstrom et al. | 424/59 U X |
| 3,983,176 | 9/1976 | Yamada et al. | 568/315 X |
| 4,024,067 | 5/1977 | Paciorek et al. | 568/315 X |

FOREIGN PATENT DOCUMENTS

| | | | |
|---|---|---|---|
| 2915439 | 10/1979 | Fed. Rep. of Germany . | |
| 2199971 | 4/1974 | France | 424/59 |
| 2236515 | 2/1975 | France | 424/59 |
| 2291745 | 6/1976 | France | 424/59 |
| 2383904 | 10/1978 | France | 424/59 |
| 2440933 | 6/1980 | France | 424/59 |
| 350461 | 1/1961 | Switzerland | 424/59 |
| 1396240 | 6/1975 | United Kingdom | 424/59 |
| 1473483 | 5/1977 | United Kingdom | 424/59 |
| 1553094 | 9/1979 | United Kingdom | 424/59 |

OTHER PUBLICATIONS

J. Willis, A. Kligman, and J. Epstein, "The Journal of Investigative Dermatology", vol. 59, No. 6, p. 416, 1973.

Primary Examiner—Dale R. Ore
Attorney, Agent, or Firm—Fleit, Jacobson, Cohn & Price

[57] ABSTRACT

A cosmetic composition is disclosed containing, as an agent for protection against light radiation, at least one 2-hydroxydibenzoylmethane of the formula:

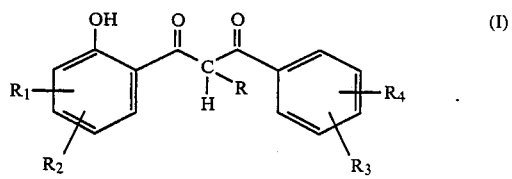

in which $R_1$, $R_2$, $R_3$ and $R_4$ independently of one another denote hydrogen or halogen atoms, a straight-chain or branched-chain $C_1$ to $C_{12}$ alkyl group or a $C_1$ to $C_4$ lower alkoxy group and R denotes a hydrogen atom or a $C_1$ to $C_4$ lower alkyl group, in a cosmetically acceptable medium.

25 Claims, No Drawings

COSMETIC COMPOSITIONS CONTAINING HYDROXYL DERIVATIVES OF DIBENZOYLMETHANE AND THEIR USE IN PROTECTING THE SKIN AGAINST ULTRAVIOLET RAYS AND DERIVATIVES FOR USE THEREIN

This application is a continuation of application Ser. No. 379,023, filed May 17, 1982, now abandoned.

The present invention relates to cosmetic compositions containing hydroxyl derivatives of dibenzoylmethane, which act as sun filters, and to the use of these compositions for protecting the skin against UV rays, and also to hydroxyl derivatives of dibenzoylmethane used in these compositions and to a process for their preparation.

It is known that light radiation between 280 and 400 nm makes it possible to tan the human epidermis and that the rays having wavelengths between 280 and 320 nm, known under the name UV.B, cause erythema and skin burns, the seriousness of which increases rapidly with the period of exposure.

Nevertheless, it has been found that, although the UV.A rays, which have a wavelength of between 320 and 400 nm, cause tanning of the skin, they can cause damage thereto, in particular in the case of sensitive skin or skin which is continually exposed to solar radiation. Furthermore, it has been found that the UV.A rays can potentiate the action of the UV.B rays, as has been described by several groups of authors and more particularly by J. WILLIS, A. KLIGMAN and J. EPSTEIN (The Journal of Investigative Dermatology, Volume 59, No. 6, page 416, 1973) under the name of "photo-enhancement".

It has therefore seemed desirable to attempt to filter out the UV.A rays as well.

It is already known to use dibenzoylmethane and derivatives thereof substituted by alkyl and/or alkoxy groups as cosmetic anti-sunburn agents for filtering out the UV.A rays. However, some of these compounds, such as dibenzoylmethane or dianisoylmethane, are sparingly soluble in the customary cosmetic oils and fats. Other compounds, such as 4-tert.-butyl-4'-methoxydibenzoylmethane, have an inadequate stability to light.

It is known, furthermore, that some constituents of cosmetic preparations, and in particular certain dyestuffs in dyeing compositions, coloured hair-lacquers, shampoos, setting lotions and make-up products, such as tinted creams, nail varnishes and lipsticks, do not always possess sufficient stability to light, and that they degrade under the action of light radiation.

Consequently, it is desirable to incorporate, into such preparations, compounds which are capable of filtering light radiation and which must have, in addition to good filtering properties, good stability and adequate solubility in the media normally used in cosmetics, and in particular in oils and fats.

In the course of our research, we have discovered surprisingly, that, certain 2-hydroxydibenzoylmethane derivatives have good filtering properties in respect of UV rays, some of them filtering UV B rays of wavelengths of between 280 and 320 nm and others filter UV A rays of wavelengths of between 320 to 400 nm.

Furthermore, these compounds have an excellent liposoluble character, very good stability to light and also very good heat stability. These compounds also have the advantage of not being toxic or irritant and of being harmless towards the skin.

These compounds disperse uniformly in conventional cosmetic carriers capable of forming a continuous film, and in particular in fatty carriers, and can thus be applied easily to the skin to form an effective protective film.

The present invention thus provides a cosmetic composition containing, as an agent for protection against light radiation, at least one 2-hydroxydibenzoylmethane of the general formula:

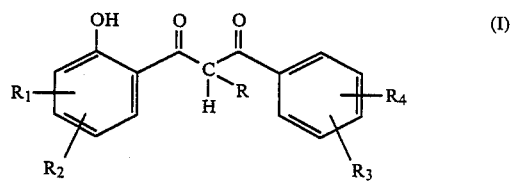

in which $R_1$, $R_2$, $R_3$ and $R_4$ independently of one another denote a hydrogen or halogen atom, a straight-chain or branched-chain $C_1$ to $C_{12}$ alkyl group or a $C_1$ to $C_4$ alkoxy group and R denotes a hydrogen atom or a $C_1$ to $C_4$ alkyl group, in a cosmetically acceptable medium.

The compounds of the formula (I) above can also be represented by the resonance formula (Ia) below:

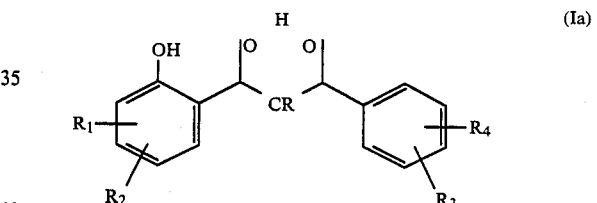

in which the various substituents have the same meaning as indicated above.

Of course, it is to be understood that when reference is made to the compound of the formula (I), this includes the compounds of the formula (Ia). Compounds in which R denotes a hydrogen atom generally absorb in the UV A region. Compounds in which R denotes a $C_1$–$C_4$ alkyl group generally absorb in the UV B region.

The present invention also provides a process for prtecting the human epidermis against solar radiation, which consists in applying, to the skin, a compound of the formula (I) above, contained in a cosmetically acceptable medium.

In formula (I) above, the halogen atom is generally a chlorine or bromine atom and is preferably a chlorine atom. The straight-chain or branched-chain $C_1$ to $C_{12}$ alkyl group is more particularly a methyl, ethyl, propyl, isopropyl, butyl, isobutyl, tert.-butyl or lauryl group and is preferably a methyl, tert.-butyl or lauryl group. The $C_1$ to $C_4$ alkoxy group more particularly denotes a methoxy, ethoxy or butoxy group. R preferably denotes a hydrogen atom or a methyl or butyl group.

Some of the compounds of the formula (I) are new.

The invention thus also provides the compounds corresponding to the formula general formula (II):

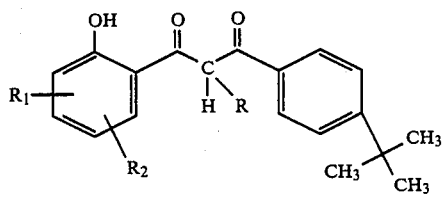 (II)

in which R, $R_1$ and $R_2$ have the same meaning as in the formula (I).

These compounds of formula (II) possess very good solubility in the fatty phases normally used in the formulation of anti-sunburn products.

Furthermore, they have the advantage that they can be prepared from easily accessible industrial starting materials, such as p-tert.-butylbenzoic acid and the acid chloride derived therefrom.

Compounds of the formula (I) which are used more particularly in the cosmetic composition of the invention are: 2-hydroxy-4'-tert.-butyldibenzoylmethane, 2-hydroxy-4-methoxy-4'-tert.-butyldibenzoylmethane, 2-hydroxy-5-methyl-4'-tert.-butyldibenzoylmethane, 2-hydroxy-5-chloro-4'-tert.-butyldibenzoylmethane, 2-hydroxy-5-chloro-2'-methoxydibenzoylmethane, 2-hydroxy-5-tert.-butyl-4'-tert.-butyldibenzoylmethane, 2-hydroxy-5-methyl-2', 6'-dimethoxydibenzoylmethane, 2-hydroxydibenzoylmethane, 2-hydroxy-4-butoxy-4'-tert.-butyldibenzoylbutylmethane, 2-hydroxy-5-lauryl-4'-tert.-butyldibenzoylmethane and 2-hydroxy-4,4'-dibutoxy-dibenzoylbutylmethane.

The wavelength corresponding to the absorption maximum of these compounds (λmax), and also their molar extinction coefficient (ε), are indicated in the table below:

| Compound | λmax CHCl₃ | ε |
| --- | --- | --- |
| 2-hydroxy-4'-tert.-butyl-dibenzoylmethane | 367 nm | 30190 |
| 2-hydroxy-4-methoxy-4'-tert.-butyldibenzoylmethane | 373 nm | 31600 |
| 2-hydroxy-5-methyl-4'-tert.-butyldibenzoylmethane | 346 nm | 22000 |
|  | 374 nm | 25100 |
| 2-hydroxy-5-chloro-4'-tert.-butyldibenzoylmethane | 345 nm | 20300 |
|  | 375 nm | 28000 |
| 2-hydroxy-5-chloro-2'-methoxydibenzoylmethane | 318 nm | 10800 |
|  | 378 nm | 26000 |
| 2-hydroxy-5-tert.-butyl-4'-tert.-butyldibenzoylmethane | 345 nm | 22200 |
|  | 372 nm | 25800 |
| 2-hydroxy-5-methyl-2',6'-dimethoxydibenzoylmethane | 322 nm | 12900 |
|  | 362 nm | 14200 |
| 2-hydroxydibenzoylmethane | 365 nm | 23600 |
| 2-hydroxy-4-butoxy-4'-tert.-butyl-dibenzoylbutylmethane | 318 nm | 9370 |
|  | 278 nm | 18410 |
| 2-hydroxy-5-lauryl-4'-tert.-butyl-dibenzoylmethane | 343 nm | 21535 |
|  | 372 nm | 24750 |
| 2-hydroxy-4,4'-dibutoxy-dibenzoyl-butylmethane | 280 nm | 37760 |

The compounds of the formula (I) used in the cosmetic composition according to the invention can be prepared by a two-step process.

The first step of the process is the condensation of a benzoyl chloride with a 2-hydroxyphenyl alkyl ketone according to the following equation:

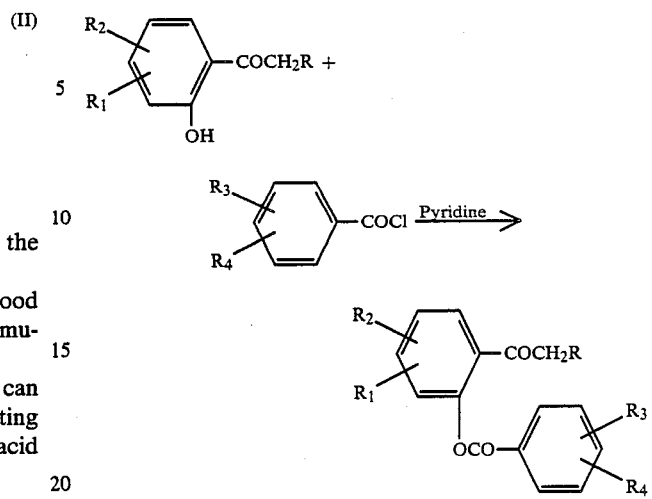

The 2-benzoyloxyphenyl alkyl ketone obtained in the first step of the process is then subjected to a Baker-Venkaterraman rearrangement according to the following equation:

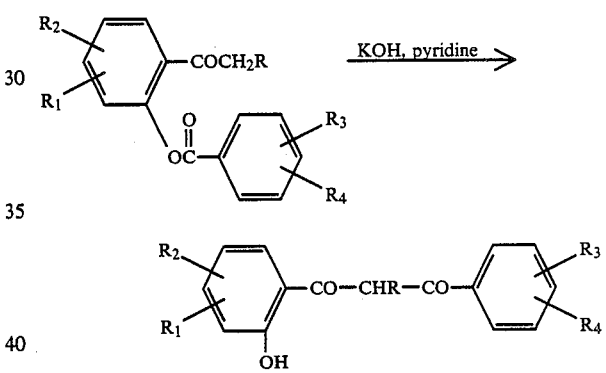

When used as compositions intended for protecting the human epidermis against ultraviolet rays, the cosmetic compositions according to the invention, containing at least one compound of the formula (I) as the agent for protection against light radiation, can be presented in a variety of forms normally used for this type of composition. In particular, they can be presented in the form of a solution, a lotion, an emulsion, such as a cream or a milk, or an aqueous-alcoholic gel, or can be packaged as an aersol.

They can contain the cosmetic adjuvants normally used in this type of composition, such as thickeners, softeners, humectants, superfatting agents, emollients, wetting agents, surface-active agents, preservatives, anti-foam agents, perfumes, oils, waxes, dyestuffs and/or pigments serving to colour the composition itself or the skin, or any other ingredient normally used in cosmetics.

The compound of the formula (I) is present, in particular, in an amount, by weight, of 0.5 to 10%, relative to the total weight of the composition.

As the solubilising solvent, it is possible to use a monoalcohol or a lower polyalcohol or a mixture thereof, or an aqueous-alcoholic solution. The monoalcohols or polyalcohols which are more particularly preferred are ethanol, isopropanol, propylene glycol or glycerol.

One embodiment of the invention is an emulsion in the form of a protective cream or milk, which comprises, in addition to the compounds of the formula (I), fatty alcohols, oxyethyleneated fatty alcohols, fatty acid esters and, in particular fatty acid triglycerides, fatty acids, lanolin, natural or synthetic oils, and waxes, in the presence of water.

Another embodiment consists of lotions, such as oily-alcoholic lotions based on a lower alcohol, such as ethanol, or a glycol, such as propylene glycol, and/or a polyol, such as glycerol, and on fatty acid esters, such as fatty acid triglycerides.

The cosmetic composition of the invention can also be in the form of an alcoholic gel comprising one or more lower alcohols, such as ethanol, propylene glycol or glycerol, and a thickener, in the presence of water.

The pesent invention also provides cosmetic anti-sunburn compositions containing at least one compound of the formula (I), which in the case where the or each compound is a UV A filter, is in association with a sun filter which absorbs the UV B rays (having wavelengths of 280 to 320 nm) which may be a compound of formula (I) according to the present invention or which may be a known UV B filter. It is thus possible to obtain a formulation which filters out substantially all the UV B and UV A radiation.

As sun filters which filter out the UV B rays, there may be mentioned water-soluble filters such as the benzylidene camphor derivatives described in French Specification Nos. 2 199 971, 2 236 515 and 2 383 904, and, more particularly, 4-(2-oxobornylidene-3-methyl)-phenyltrimethylammonium methylsulphate, 4-(2-oxobornylidene-3-methyl)-benzenesulphonic acid salts, 2-methyl-5-(2-oxobornylidene-3-methyl)benzenesulphonic acid salts and 2-phenylbenzimidazole-5-sulphonic acid salts.

The compounds according to the invention can also be used in association with UV B filters which are liposoluble compounds or oils having sun-filtering properties, such as, coffee bean oil. As lipophilic UV B sun filters, there may be mentioned in particular, salicylic acid derivatives, such as 2-ethylhexyl salicylate and homomenthyl salicylate, cinnamic acid derivatives, such as 2-ethylhexyl p-methoxycinnamate and 2-ethoxyethyl p-methoxycinnamate, p-aminobenzoic acid derivatives, such as amyl p-aminobenzoate and 2-ethylhexyl p-dimethylaminobenzoate, benzophenone derivatives, such as 2hydroxy-4-methoxybenzophenone 2,2'-dihydroxy-4-methoxybenzophenone, and camphor derivatives, such as 3-(4-methylbenzylidene)-camphor, optionally in association with 4-isopropyldibenzoylmethane, and 3-benzylidenecamphor.

These anti-sunburn compositions can be presented in the form of, for example, a solution, a lotion, an emulsion, such as a cream or a milk, an oil, a greasy gel or an aqueous-alcoholic or alcoholic gel, or can be packaged as an aerosol. They can contain the abovementioned cosmetic adjuvants normally used in this type of composition.

If the compositions are presented in the form of an emulsion, it is possible to use a water-soluble UV.B filter dissolved in the aqueous phase, the compound of the formula (I) being dissolved in the fatty phase.

If the anti-sunburn composition is in the form of an oil, it contains, in addition to the compounds of the formula (I), a fatty phase consisting of, say, one or more fatty acid esters, such as fatty acid triglycerides, natural or synthetic waxes, natural or synthetic oils and lanolin.

The present invention provides cosmetic compositions containing at least one compound of the formula (I) as an agent for protection against ultraviolet rays, the said compositions being compositions for the hair, such as hair lacquers, setting lotions optionally having treatment properties or disentangling properties, shampoos, colouring shampoos and hair-dyeing compositions, as well as make-up products, such as nail varnishes, treatment creams for the epidermis, make-up foundations and lipsticks, and also any other cosmetic composition which, because of its constituents, can present problems of stability to light during storage.

The following Examples further illustrate the present invention.

The compounds of the formula (II) according to the invention can be prepared by the two-step process described above. The first step of the process is the condensation of p-tert.-butylbenzoyl chloride with a 2-hydroxyphenylalkylketone in pyrindine. The 2-p-tert.-butylbenzoyloxyphenylalkylketone obtained is then subjected to a Baker-Venkaterraman rearrangement in pyridine, in the presence of potassium hydroxide.

EXAMPLE 1

Process for the preparation of 2-hydroxy-4'-tert.-butyldibenzoylmethane.

1st step: Preparation of 2-para-tert.-butylbenzoyloxyacetophenone.

Starting materials:
  2-Hydroxyacetophenone 1,130 g (8.3 mols)
  Pyridine dried over a molecular sieve 3,320 ml
  Para-tert.-butylbenzoyl chloride 1,691 g (8.6 mols)
  35.5% strength hydrochloric acid 12 liters
  Ethanol (recrystallised) 3 liters Procedure The pyridine and the 2-hydroxyacetophenone are introduced into a reactor equipped with a thermometer, a dropping funnel, a mechanical stirrer and a condenser. This solution is heated to 60°–70° C. and the para-tert.-butylbenzoyl chloride is added dropwise. A precipitate of pyridine hydrochloride forms. After the addition has ended, the mixture is heated at 80° C. for ¼ hour. It is cooled and a solution of 30 liters of water and 12 liters of 35.5% strength HCl is added in small portions, the reactor being cooled with an ice bath. A pink precipitate forms. It is filtered off, washed with water until the pH of the washings is neutral, and recrystallised from 3 liters of ethanol.

The product is dried in vacuo in the presence of $P_2O_5$.

Weight obtained 2,111 g
  Theoretical weight 2,460 g
  Yield 85.8%
  Appearance: Pale pink powder.

The purity of the benzoate obtained is checked by thin layer chromatography:eluant:chloroform, silica plate. A single spot is obtained.

2nd step: Preparation of 2-hydroxy-4'-tert.-butyldibenzoylmethane.

Starting materials
  2-para-tert.-butylbenzoyloxyacetophenone 20.75 g (7 mols)
  Ground potassium hydroxide 5,090 g (about 91 mols)
  Pyridine died over KOH 8.28 liters
  Hexane 20 liters
  Hydrochloric acid 12.5 liters of 35.5% strength Procedure The 2-para-tert.-butylbenzoyloxyacetophenone and the pyridine are introduced into a reactor equipped with a thermometer, a condenser, a stirrer and a dropping funnel. The ground potassium hydroxide is introduced in portions. The reaction exothermic; the reactor is cooled when the temperature exceeds 45° C. The reaction medium becomes very pasty. After the introduction of the potassium hydroxide has ended, the mixture is stirred for 4 hours at ambient temperature. A solution of 12.5 liters of 35.5% strength hydrochloric acid and 37.5 liters of water is then added by means of the dropping funnel, the reactor being cooled. This introduction is regulated so that the temperature of the reaction medium is not above 60°–65° C. The mixture is stirred for 1 hour at above 15° C. so that the expected product crystallises well. The product is filtered off, washed with water until the pH of the washings is neutral, and dried in vacuo in the presence of $P_2O_5$.

The powder obtained is recrystallised from 7 to 10 liters of hexane. The purity of the product is checked by thin layer chromatography (eluant: $CHCl_3$). The two experiments carried out in the laboratory required two recrystallisations from hexane.

Weight obtained 1,535 kg
Theoretical weight 2,074 kg
Yield 74%
Elementary analysis: Theory C=77.0%; H=6.8%; Found C=76.9%; H=6.9%; Melting point=120° C.

The process for the preparation of other new compounds according to the invention is summarised in the table which follows.

is added to the aqueous phase, with vigorous stirring; the vigorous stirring is maintained for 10 to 15 minutes, the mixture is left to cool to about 40° C., with moderate stirring, and the perfume is added.

EXAMPLE 9

Sun Milk

This composition is identical to that of Example 8, except that 2.5% of 3-benzylidenecamphor, which is soluble in the fatty phase, is added to the latter.

EXAMPLE 10

Protective Day-Cream

Triglycerides of fatty acids ($C_8$ to $C_{12}$) 31.0 g
Glycerol monostearate 6.0 g
Stearic acid 2.0 g
Cetyl alcohol 1.2 g
Lanolin 4.0 g
Preservative 0.3 g
2-Hydroxy-4'-tert.-butyldibenzoylmethane 3.0 g
Propylene glycol 2.0 g
Triethanolamine 0.5 g
Perfume 0.5 g
Demineralised water q.s.p. 100 g This composition is prepared in the same manner as the protective milk of Example 8.

EXAMPLE 11

Sun Cream

This composition is identical to that of Example 10,

| Example No | Compound | Starting phenylalkylketone | C theory / C found | H theory / H found | Cl theory / Cl found | Melting Point | Yield |
|---|---|---|---|---|---|---|---|
| 2 | 2-Hydroxy-4-methoxy-4'-tert.-butyldibenzoylmethane | 2-Hydroxy-4-methoxy-acetophenone | 73.6 / 73.7 | 6.8 / 6.8 | | 120° C. | 63% |
| 3 | 2-Hydroxy-5-methyl-4'-tert.-butyldibenzoylmethane | 2-Hydroxy-5-methyl-acetophenone | 77.4 / 77.2 | 7.1 / 7.2 | | 114° C. | 66.5% |
| 4 | 2-Hydroxy-5-chloro-4'-tert.-butyldibenzoylmethane | 2-Hydroxy-5-chloro-acetophenone | 69.0 / 68.9 | 5.8 / 5.8 | 10.7 / 10.8 | 117° C. | 69.5% |
| 5 | 2-Hydroxy-5-tert.-butyl-4'-tert.-butyldibenzoylmethane | 2-Hydroxy-5-tert.-butyl-acetophenone | 78.4 / 78.3 | 8.0 / 8.0 | | 115° C. | 74.5% |
| 6 | 2-Hydroxy-4-butoxy-4'-tert.-butyl-dibenzoylbutylmethane | 2-Hydroxy-4-butoxy-phenylpentylketone | 76.38 / 76.44 | 8.55 / 8.60 | | an oil | 35% |
| 7 | 2-Hydroxy-5-lauryl-4'-tert.-butyl-dibenzoylmethane | 2-Hydroxy-5-lauryl-acetophenone | 80.13 / 80.21 | 9.54 / 9.48 | | an oil | 45% |

EXAMPLE 8

Protective Milk

Cetyl/stearyl alcohol 2.0 g
Cetyl alcohol 2.0 g
Triglycerides of fatty acids ($C_8$ to $C_{12}$) 20.0 g
Lanolin 4.0 g
Stearic acid 0.5 g
Silicone oil 0.3 g
2-Hydroxydibenzoylmethane 1.0 g
Preservative 0.3 g
Carbopol 934 (crosslinked polyacrylic acid sold by GOODRICH CHEMICAL) 0.15 g
Triethanolamine 0.20 g
Perfume 0.40 g
Demineralised water q.s.p. 100 g To prepare this emulsion, the fatty substances are heated to about 80°–85° C.; the filter of the formula (I) is added.

In a separate operation, the water and the watersoluble compounds are heated to 80°–85° C. The fatty phase except that 3% of 2-ethylhexyl p-dimethylaminobenzoate, which is soluble in the fatty phase, is added to the latter.

EXAMPLE 12

Protective Day-Cream

Polyoxyethyleneated fatty alcohols 7.0 g
Fatty acid triglycerides 30.0 g
Glycerol monostearate 2.0 g
Silicone oil 1.5 g
Cetyl alcohol 1.5 g
Preservative 0.3 g
2-Hydroxy-5-methyl-4'-tert.-butylibenzoylmethane 3.0 g
Perfume 0.5 g
Demineralised water q.s.p. 100 g

EXAMPLE 13

Sun Cream

This composition is identical to the that of Example 12, except that 3% of 4-(2-oxobornylidene-3-methyl)-phenyltrimethylammonium methyl-sulphate, which is soluble in the aqueous phase, is added to the latter.

EXAMPLE 14

Oily-Alcoholic Sun Lotion

The following ingredients are mixed, if necessary with heating to about 40°–45° C. in order to homogenise them:

2-Hydroxy-4-methoxy-4'-tert.-butyldibenxoylmethane 2.50 g
3-benzylidenecamphor 2 g
Perfume 0.50 g
96° strength ethanol 47.50 g
Triglycerides of fatty acids ($C_8$ to $C_{12}$) 47.50 g

EXAMPLE 15

Sun Oil

The following ingredients are mixed, more conveniently with heating to about 40°–45° C. in order to homogenise them:

2-Hydroxy-5-chloro-2'-methoxydibenzoylmethane 2 g
2-Ethylhexyl p-dimethylaminobenzoate 2 g
Cacao butter 2.5 g
Antioxidant 0.05 g
Perfume 0.5 g
Triglycerides of fatty acids ($C_8$ to $C_{12}$) q.s.p. 100 g

EXAMPLE 16

Greasy Sun Gel

2-Hydroxy-5-tert.-butyl-4'-tert.butyldibenzoylmethane 3.00 g
2-Ethylhexyl p-methoxycinnamate 2 g
Cacao butter 5.00 g
Antioxidant 0.05 g
Silica 10.00 g
Perfume 1.00 g
Triglycerides of fatty acids ($C_8$ to $C_{12}$) q.s.p. 100 g This greasy gel is prepared by heating the fatty substances to about 40°–45° C. and then adding the silica, with stirring, and allowing to cool.

EXAMPLE 17

Alcoholic Protective Gel

Carbopol 934 (crosslinked polyacrylic acid sold by GOODRICH CHEMICAL) 0.70 g
Triethanolamine 0.35 g
Propylene glycol 25.00 g
96° strength ethanol 25.00 g
2-Hydroxy-5-chloro-4'-tert.butyldibenzoylmethane 2.00 g
Preservative 0.30 g
Perfume 0.40 g
Demineralised water q.s.p. 100 g To prepare this aqueous-alcoholic gel, the Carbopol is dispersed in the water, with vigorous stirring, and the triethanolamine is then added, followed by the solvents (propylene glycol and 96° strength ethanol), in which the filter of the formula (I) has been dissolved beforehand.

EXAMPLE 18

Protective Day-Cream ($C_8$ to $C_{12}$) Fatty acid triglycerides 31.0 g
Glycerol monostearate 6.0 g
Stearic acid 2.0 g
Cetyl alcohol 1.2 g
Lanolin 4.0 g
Preservative 0.3 g
2-Hydroxy-5-lauryl-4'-tert.butyldibenzoylmethane 3.0 g
Propylene glycol 2.0 g
Triethanolamine 0.5 g
Perfume 0.5 g
Demineralised water q s p 100 g This composition is prepared in the same manner as the protective milk of Example 8.

EXAMPLE 19

Sun Oil

The following ingredients are mixed, if necessary with heating to about 40°–45° C. in order to homogenise them:

2-Hydroxy-4-butoxy-4'-tert.-butyldibenzoylbutylmethane 4 g
Cocoa butter 2.5 g
Antioxidant 0.05 g
Perfume 0.5 g
($C_8$ to $C_{12}$) Fatty acid triglycerides q s p 100 g

EXAMPLE 20

Greasy Sun Gel

2-Hydroxy-5-tert.-butyl-4'-tert.-butyldibenzoyl methane 3 g
2-Hydroxy-4-butoxy-4'-tert.-butyldibenzoylbutylmethane 2 g
Cocoa butter 5 g
Antioxidant 0.05 g
Silica 10 g
Perfume 1 g
($C_8$ to $C_{12}$) Fatty acid triglycerides q s p 100 g This greasy gel is prepared by heating the fatty substances to about 40°–45° C. and then adding the silica, with stirring, and allowing to cool.

EXAMPLE 21

Oily-Alcoholic Sun Lotion

The following ingredients are mixed, if necessary with heating to about 40° to 45° C. in order to homogenise them:

2-Hydroxy-4,4'-dibutoxydibenzoylbutylmethane 4.5 g
Perfume 0.5 g
96° Strength ethanol 47.5 g
($C_8$–$C_{12}$) Fatty acid triglycerides 47.5 g

EXAMPLE 22

Sun Cream

Polyoxyethyleneated fatty alcohols 7.0 g
Fatty acid triglycerides 30.0 g
Glycerol monostearate 2.0 g
Silicone oil 1.5 g
Cetyl alcohol 1.5 g
Preservative 0.3 g
2-Hydroxy-5-methyl-4'-tert.-butyldibenzoylmethane 2.0 g 2-Hydroxy-4,4'-dibutoxydibenzoylbutylmethane 2.0 g
Perfume 0.5 g
Demineralised water q s p 100 g

We claim:

1. A composition for protecting the skin against UV-light radiation in the range of about 280 to 400 nm which comprises, at least one 2-hydroxydibenzoylmethane of the formula:

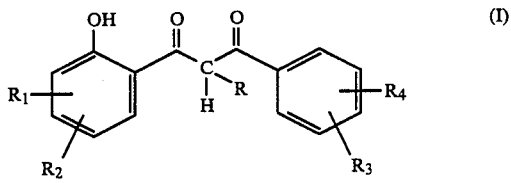

in which $R_1$, $R_2$, $R_3$ and $R_4$ independently of one another denote a hydrogen or halogen atom, a straight-chain or branched-chain alkyl group of up to 12 carbon atoms or a $C_1$ to $C_4$ alkoxy group and R denotes a hydrogen atom or a $C_1$ to $C_4$ alkyl group, in a cosmetically acceptable medium, said at least one 2-hydroxydibenzoylmethane being present in an amount of about 0.5 to 10% by weight of said composition, and said composition being in a form selected from the group consisting of a lotion, an emulsion, an aqueous-alcoholic gel, an alcoholic gel, and an aerosol, and containing at least one cosmetic adjuvant selected from the group consisting of thickeners, softeners, superfatting agents, humectants, wetting agents, surface-active agents, preservatives, antifoam agents, perfumes, oils, waxes, dyestuffs and pigments.

2. A composition according to claim 1, in which the halogen is chlorine, the straight-chain or branched-chain alkyl group is a methyl, ethyl, propyl, isopropyl, butyl, isobutyl, tert.-butyl or lauryl group, the alkoxy group is a methoxy, ethoxy or butoxy group and R denotes a hydrogen atom or a methyl or butyl group.

3. A composition according to claim 1 which contains a 2-hydroxydibenzoylmethane of formula (I) in which R denotes a hydrogen atom.

4. A composition according to claim 3, which contains a 2-hydroxydibenzoylmethane selected from the group consisting of
2-hydroxy-4'-tert.-butyldibenzoylmethane,
2-hydroxy-4-methoxy-4'-tert.-butyldibenzoylmethane,
2-hydroxy-5-methyl-4'-tert.-butyldibenzoylmethane,
2-hydroxy-5-chloro-4'-tert.-butyldibenzoylmethane,
2-hydroxy-5-chloro-2'-methoxydibenzoylmethane,
2-hydroxy-5-tert.-butyl-4'-tert.-butyldibenzoylmethane,
2-hydroxy-5-methyl-2',6'-dimethoxydibenzoylmethane,
2-hydroxydibenzoylmethane and 2-hydroxy-5-lauryl-4'-tert.-butyl-dibenzoylmethane.

5. A composition according to claim 1 which contains a 2-hydroxydibenzoylmethane of formula (I) in which R denotes a $C_1$-$C_4$ alkyl group.

6. A composition according to claim 1, which is in the form of an anti-sunburn composition, and which contains a 2-hydroxydibenzoylmethane of formula (I) in which R denotes a hydrogen atom together with a watersoluble or liposoluble sun filter having a filtering action in respect of UV.B rays which is selected from the group consisting of benzylidenecamphor derivatives, coffee bean oil, salicylic acid derivatives, cinnamic acid derivatives, p-aminobenzoic acid derivatives and benzophenone derivatives.

7. A composition according to claim 1, which is in the form of an anti-sunburn composition and which contains a 2-hydroxydibenzoylmethane of formula (I) in which R denotes a $C_1$-$C_4$ alkyl group and optionally a 2-hydroxydibenzoylmethane of formula (I) in which R denotes a hydrogen atom.

8. A composition according to claim 1 which is in the form of an emulsion, and wherein said cosmetically acceptable medium contains fatty alcohols, oxyethyleneated fatty alcohols, fatty acid esters, fatty acids, lanolin, natural or synthetic oils and waxes, in the presence of water.

9. A composition for protecting the skin against UV-light radiation in the range of about 280 to 400 nm which comprises, at least one 2-hydroxydibenzoylmethane of the formula:

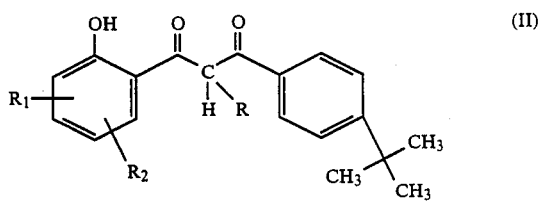

in which $R_1$ and $R_2$ independently of one another denote a hydrogen or halogen atom, a straight-chain or branched-chain alkyl group of up to 12 carbon atoms or a $C_1$ to $C_4$ alkoxy group and R denotes a hydrogen atom or a $C_1$ to $C_4$ alkyl group, in a cosmetically acceptable medium, said at least one 2-hydroxydibenzoylmethane being present in an amount of about 0.5 to 10% by weight of said composition, and said composition being in a form selected from the group consisting of a lotion, an emulsion, an aqueous-alcoholic gel, an alcoholic gel, and an aerosol, and containing at least one cosmetic adjuvant selected from the group consisting of thickeners, softeners, superfatting agents, humectants, wetting agents, surface-active agents, preservatives, antifoam agents, perfumes, oils, waxes, dyestuffs and pigments.

10. A composition for protecting the skin against UV-light radiation in the range of about 280 to 400 nm which comprises, at least one 2-hydroxydibenzoylmethane selected from the group consisting of
2-hydroxy-4'-tert.-butyldibenzoylmethane,
2-hydroxy-4-methoxy-4'-tert.-butyldibenzoylmethane,
2-hydroxy-5-methyl-4'-tert.-butyldibenzoylmethane,
2-hydroxy-5-chloro-4'-tert.-butyldibenzoylmethane,
2-hydroxy-5-chloro-2'-methoxydibenzoylmethane,
2-hydroxy-5-tert.-butyl-4'-tert.-butyldibenzoylmethane,
2-hydroxy-5-methyl-2',6'-dimethoxydibenzoylmethane,
2-hydroxy-5-lauryl-4'-tert.-butyl-dibenzoylmethane,
2-hydroxy-4-butoxy-4'-tert.-butyldibenzoylbutylmethane and
2-hydroxy-4,4'-dibutyloxydibenzoylbutylmethane,
in a cosmetically acceptable medium, said at least one 2-hydroxydibenzoylmethane being present in an amount of about 0.5 to 10% by weight of said composition, and said composition being in a form selected from the group consisting of a lotion, an emulsion, an aqueous-alcoholic gel, an alcoholic gel, and an aerosol, and containing at least one cosmetic adjuvant selected from the group consisting of thickeners, softeners, superfatting agents, humectants, wetting agents, surface-active agents, preservatives, antifoam agents, perfumes, oils, waxes, dyestuffs and pigments.

11. Process for protecting the human epidermis aganist UV rays in the range of about 280 to 400 nm, which comprises applying thereto an amount of about 0.5 to 10% by weight of a 2-hydroxydibenzoylmethane of the formula:

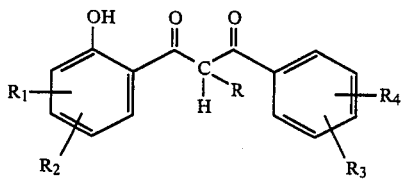

(I)

in which $R_1$, $R_2$, $R_3$ and $R_4$ independently of one another denote a hydrogen or halogen atom, a straight-chain or branched-chain alkyl group of up to 12 carbon atoms or a $C_1$ to $C_4$ alkoxy group and R denotes a hydrogen atom or a $C_1$ to $C_4$ alkyl group, in a cosmetically acceptable medium.

12. Process according to claim 11, which comprises applying to the human epidermis a 2-hydroxydibenzoylmethane of formula (I) wherein the halogen is chlorine, the straight-chain or branched-chain alkyl group is a methyl, ethyl, propyl, isopropyl, butyl, isobutyl, tert.-butyl or lauryl group, the alkoxy group is a methoxy, ethoxy or butoxy group and R denotes a hydrogen atom or a methyl or butyl group.

13. Process according to claim 11, wherein R denotes a hydrogen atom.

14. Process according to claim 11, which contains a 2-hydroxydibenzoylmethane selected from the group consisting of
2-hydroxy-4'-tert.-butyldibenzoylmethane,
2-hydroxy-4-methoxy-4'-tert.-butyldibenzoylmethane,
2-hydroxy-5-methyl-4'-tert.-butyldibenzoylmethane,
2-hydroxy-5-chloro-4'-tert.-butyldibenzoylmethane,
2-hydroxy-5-chloro-2'-methoxydibenzoylmethane,
2-hydroxy-5-tert.-butyl-4'-tert.-butyldibenzoylmethane,
2-hydroxy-5-methyl-2',6'-dimethoxydibenzoylmethane, and 2-hydroxy-5-lauryl-4'-tert.-butyl-dibenzoylmethane.

15. Process according to claim 11 which contains a 2-hydroxybidenzoylmethane of formula (I) in which R denotes a hydrogen atom together with a water-soluble or liposoluble sun filter having a filtering action in respect to UV-B rays which is selected from the group consisting of benzylidenecamphor derivatives, coffee bean oil, salicylic acid derivatives, cinnamic acid derivatives, p-aminobenzoic acid derivatives and benzophenone derivatives.

16. Process according to claim 11 which contains a 2-hydroxydibenzoylmethane of formula (I) in which R denotes a $C_1$–$C_4$ alkyl group and optionally a 2-hydroxydibenzoylmethane of formula (I) in which R denotes a hydrogen atom.

17. A compound which corresponds to the formula:

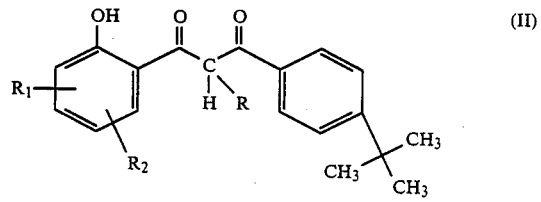

(II)

in which $R_1$ and $R_2$ independently of one another denote a hydrogen or halogen atom, a straight-chain or branched-chain alkyl group of up to 12 carbon atoms or a $C_1$ to $C_4$ alkoxy group and R denotes a hydrogen atom or a $C_1$–$C_4$ alkyl group.

18. A compound according to claim 17, in which the halogen is chlorine, the straight-chain or branched-chain alkyl group is methyl, ethyl, propyl, isopropyl, butyl, isobutyl, tert.-butyl or lauryl group, the alkoxy group is a methoxy, ethoxy or butoxy group and R denotes a hydrogen atom or a methyl or butyl group.

19. 2-Hydroxy-4'-tert.-butyldibenzoylmethane.
20. 2-Hydroxy-4-methoxy-4'-tert.-butyldibenzoylmethane.
21. 2-Hydroxy-5-methyl-4'-tert.-butyl-dibenzoylmethane.
22. 2-Hydroxy-5-chloro-4'-tert.-butyldibenzoylmethane.
23. 2-Hydroxy-5-tert.-butyl-4'-tert.-butyldibenzoylmethane.
24. 2-Hydroxy-4-butoxy-4'-tert.-butyldibenzoylmethane.
25. 2-Hydroxy-5-lauryl-4'-tert.-butyldibenzoylmethane.

* * * * *